(12) United States Patent
Yershov et al.

(10) Patent No.: US 7,288,227 B2
(45) Date of Patent: Oct. 30, 2007

(54) BIOCHIP READER WITH ENHANCED ILLUMINATION AND BIOARRAY POSITIONING APPARATUS

(75) Inventors: Gennadiy Yershov, Hinsdale, IL (US); Oleg Alferov, Woodridge, IL (US); Alexander Kukhtin, Hinsdale, IL (US)

(73) Assignee: UChicago Argonne LLC, Chicago, IL (US)

( * ) Notice: Subject to any disclaimer, the term of this patent is extended or adjusted under 35 U.S.C. 154(b) by 913 days.

(21) Appl. No.: 10/619,284

(22) Filed: Jul. 14, 2003

(65) Prior Publication Data

US 2004/0077099 A1 Apr. 22, 2004

Related U.S. Application Data

(62) Division of application No. 10/139,842, filed on May 6, 2002, now Pat. No. 6,620,623.

(51) Int. Cl.
*G01N 21/64* (2006.01)

(52) U.S. Cl. .................. 422/82.11; 250/458.1; 250/461.1; 422/82.05; 422/82.06; 422/82.08; 422/82.09; 422/104; 436/172

(58) Field of Classification Search ............ 250/458.1, 250/459.1, 461.1–461.2; 356/417; 359/385, 359/391; 422/82.05–82.11, 104; 436/86, 436/94, 172
See application file for complete search history.

(56) References Cited

U.S. PATENT DOCUMENTS 3,705,048 A * 12/1972 Staunton .................... 427/2.11

(Continued)

OTHER PUBLICATIONS

"Manufacturing DNA microarrays of high spot homogeneity and reduced background signal", Nucleic Acids Research, 2001, vol. 29, No. 7, e38, 5-pages.

*Primary Examiner*—Arlen Soderquist
(74) *Attorney, Agent, or Firm*—Joan Pennington

(57) ABSTRACT

A method of illumination and illumination apparatus are provided in a biochip reader. Illumination is provided by a non-collimated laser source or a light emitting diode (LED). The light is directed to opposing sides of a glass substrate by a pair of optical fiber bundles. The glass substrate carries a bioarray. Each of the optical fiber bundles are splayed out to make a fan, the fan being one fiber thick and defining a line of optical fiber faces. This process randomizes any non-uniformity in the illumination source, creating a more uniform illumination source. A respective divergent diffuser engages each row of optical fiber faces coupling and diffusing light substantially evenly through the opposing sides of the glass substrate to illuminate the bioarray supported by the glass substrate. The glass substrate functions as a secondary light guide. The divergent diffusers separate the optical fiber faces from the edges of the glass substrate, protecting the optical fibers from mechanical damage. A glass holder supports the glass substrate carrying the bioarray. The glass holder including a plastics springs member in spring contact engagement with the glass substrate for positioning said bioarray in a focal plane. Light also can be directed to opposing ends of the glass substrate by a second pair of optical fiber bundles. Also a single optical fiber bundle can be used to direct light in one side of the glass substrate or three optical fiber bundles can be used to direct light into the glass substrate. This method of illumination provides a superior signal to noise ratio as compared with conventional illumination systems.

5 Claims, 7 Drawing Sheets

U.S. PATENT DOCUMENTS

| | | | | |
|---|---|---|---|---|
| 4,159,875 A | * | 7/1979 | Hauser | 356/244 |
| 4,427,294 A | * | 1/1984 | Nardo | 356/344 |
| 4,608,344 A | * | 8/1986 | Carter et al. | 436/34 |
| 4,729,067 A | * | 3/1988 | Ohe | 362/26 |
| 4,977,725 A | * | 12/1990 | Gerrans et al. | 53/501 |
| 5,037,614 A | * | 8/1991 | Makita et al. | 422/68.1 |
| 5,098,676 A | * | 3/1992 | Brooks, Jr. | 422/292 |
| 5,249,077 A | | 9/1993 | Laronga et al. | |
| 5,320,808 A | * | 6/1994 | Holen et al. | 422/64 |
| 5,671,084 A | * | 9/1997 | Kurtz | 359/362 |
| 5,677,196 A | * | 10/1997 | Herron et al. | 436/518 |
| 5,781,337 A | * | 7/1998 | Pfeifer | 359/391 |
| 5,831,763 A | * | 11/1998 | Meyer | 359/391 |
| 6,271,042 B1 | | 8/2001 | Watson, Jr. et al. | |
| 6,394,409 B1 | * | 5/2002 | Chen et al. | 248/694 |
| 6,902,702 B1 | * | 6/2005 | Winegarden et al. | 422/100 |
| 2003/0138353 A1 | * | 7/2003 | Bargoot et al. | 422/58 |
| 2003/0203492 A1 | * | 10/2003 | Sillman | 436/46 |

* cited by examiner

200

210

220

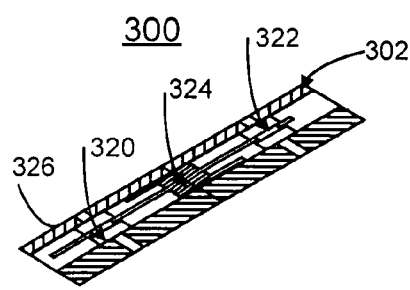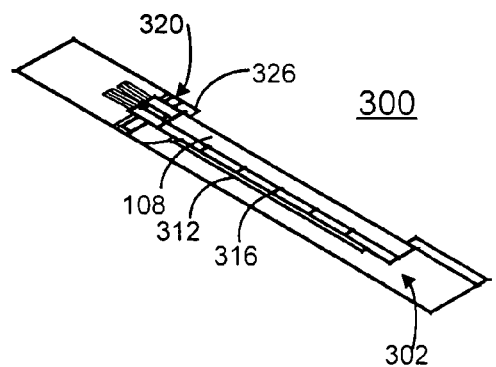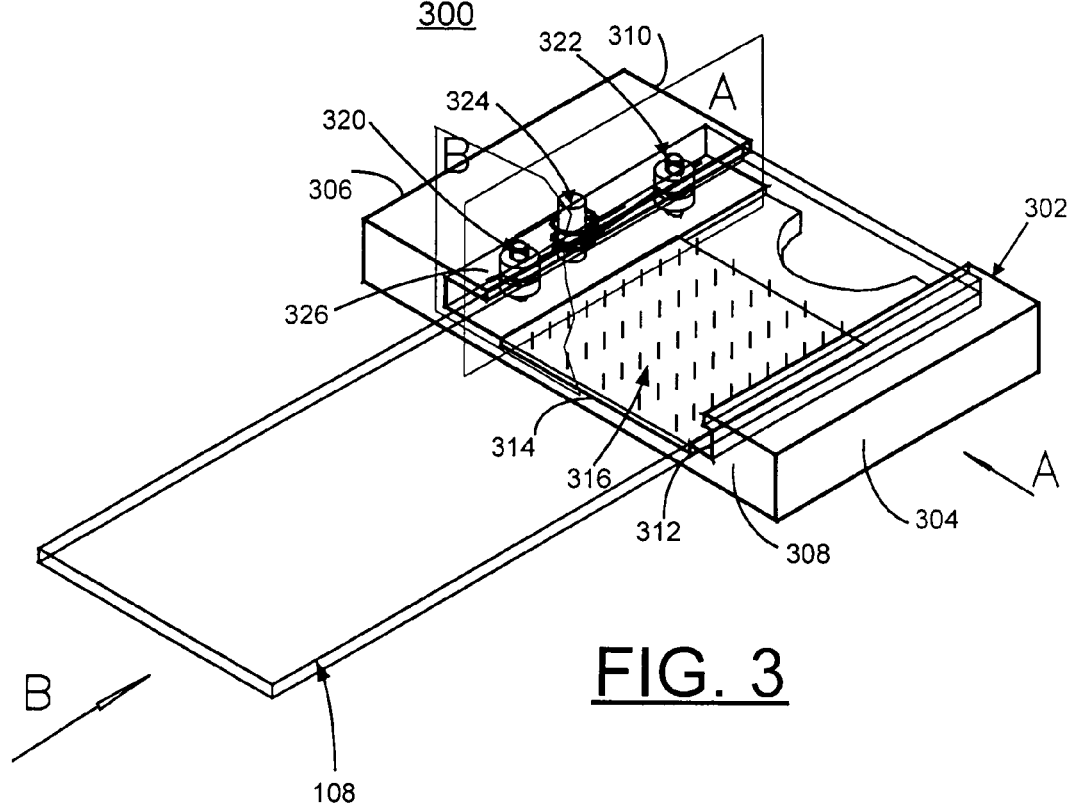

BIOCHIP READER WITH ENHANCED ILLUMINATION AND BIOARRAY POSITIONING APPARATUS

This application is a divisional application of Ser. No. 10/139,842 filed on May 6, 2002. now U.S. Pat. No. 6,620,623.

CONTRACTUAL ORIGIN OF THE INVENTION

The United States Government has rights in this invention pursuant to Contract No. W-31-109-ENG-38 between the United States Government and Argonne National Laboratory.

FIELD OF THE INVENTION

The present invention relates to a biochip reader having a novel method of illumination and improved illumination and bioarray positioning apparatus for enhanced quantitative analysis of biochip data.

DESCRIPTION OF THE RELATED ART

Analysis of biochip or bioarray data is carried out by the detection of the fluorescence from labeled target molecules that specifically interact with an immobilized array of molecular probes. The molecular probes may be attached directly onto a glass substrate or the probes may be attached onto a transparent plastic substrate. In an Argonne National Laboratory (ANL) 3D bioarray, the arrayed probes are attached to the glass substrate through a porous carrier which is chemically bound to the glass substrate.

One of the major problems in the quantitative analysis of bioarray data is finding a method of illumination of the array that is uniform over the area of the array to be analyzed. Any non-uniformity in the illumination translates into differences in the intensity of the fluorescence and thus tends to lead to erroneous results.

Another problem is positioning a glass substrate within an optical pathway so that the bioarray will be in the focal plane of a lens/lens array and within the field of view of the reader's optical system. Positioning the glass substrate has to be done repeatedly and with ease, without causing damage to the bioarray or the glass substrate. Positioning the glass substrate should not depend on the regular microscopic glass substrate thickness variation, typically, for example, 0.97 mm to 1.1 mm and also, length and width variations, length typically, for example, 75.513 mm to 76.2 mm, and width typically, for example, 24.638 mm to 25.552 mm. Information about commercially available microscope slides can be obtained, for example, at http://www.corning.com; and http://www.tedpella.com/histo_html/slides.htm. Positioning the glass substrate should not depend on whether or not a bioarray is covered with a reaction chamber. Reaction chamber information can be obtained, for example, at http://www.gracebio.com; http://www.eppendorf.com; http://www.mjr.com; and http://www.fishersci.com.

A need exists for an improved method of illumination and illumination apparatus to enable enhanced quantitative analysis of biochip data. It is desirable to provide such method of illumination and illumination apparatus that is effective and that is generally inexpensive, portable, lightweight, and simple to implement.

A need exists for an improved mechanism for positioning a glass substrate within an optical pathway so that the bioarray will be in the focal plane and within the field of view of an optical system. It is desirable to provide such an improved mechanism that is easy to use without causing any damage to the bioarray or the glass substrate.

SUMMARY OF THE INVENTION

A principal object of the present invention is to provide a biochip reader having an enhanced method of illumination and improved illumination and bioarray positioning apparatus enabling enhanced quantitative analysis of bioarray data. Other important objects of the present invention are to provide a method and apparatus for illumination in a biochip reader substantially without negative effect; and that overcome some disadvantages of prior art arrangements.

In brief, a novel method of illumination and illumination and bioarray positioning apparatus are provided in a biochip reader. Illumination is provided, for example, by a non-collimated laser source or a diode source. The light is directed to opposing sides of a glass substrate by a pair of optical fiber bundles. The glass substrate carries a bioarray. Each of the optical fiber bundles are splayed out to make a fan, the fan being one fiber thick and defining a line of optical fiber faces. This process randomizes any non-uniformity in the illumination source, creating a more uniform illumination of the bioarray. A respective divergent diffuser is provided proximate to each row of optical fiber faces coupling and diffusing light substantially evenly through the opposing sides of the glass substrate to illuminate the bioarray supported by the glass substrate.

The biochip reader includes illumination apparatus, a glass holder, and an optical system. The glass holder supports and aligns the glass substrate carrying the bioarray with the optical system. The glass holder includes a plastic springs member in contact engagement with the glass substrate with low contact forces for positioning the bioarray in a focal plane of the optical system.

In accordance with features of the invention, a manual positioner is coupled to the glass holder for simply positioning the bioarray within the field of view of an optical system. The divergent diffusers separate the optical fiber faces from the edges of the glass substrate, protecting the optical fibers from mechanical damage. A second function of the divergent diffusers is to reflect back outwardly going light to the glass to increase illumination efficiency. The glass substrate functions as a secondary light guide. The optical fiber bundles directing the laser light to the glass substrate are, for example, borosilicate fiber light guides. The optical fiber bundles also can be, for example, quartz, or plastic fiber light guides. Light also can be directed to opposing ends of the glass substrate by a second pair of optical fiber bundles. Also a single optical fiber bundle can be used to direct light in one side of the glass substrate or three optical fiber bundles can be used to direct light into the glass substrate. The method of illumination of the invention provides a superior signal to noise ratio as compared with conventional illumination systems.

BRIEF DESCRIPTION OF THE DRAWINGS

The present invention together with the above and other objects and advantages may best be understood from the following detailed description of the preferred embodiments of the invention illustrated in the drawings, wherein:

FIG. 3 is a perspective view of a glass holder for precisely positioning a glass supporting a biochip gel array used with the biochip illumination apparatus in accordance with the preferred embodiment;

FIG. 4 is a sectional view taken along line A-A of FIG. 3;

FIG. 5 is a sectional view taken along line B-B of FIG. 3; and

DETAILED DESCRIPTION OF THE PREFERRED EMBODIMENTS

Figure 1A:
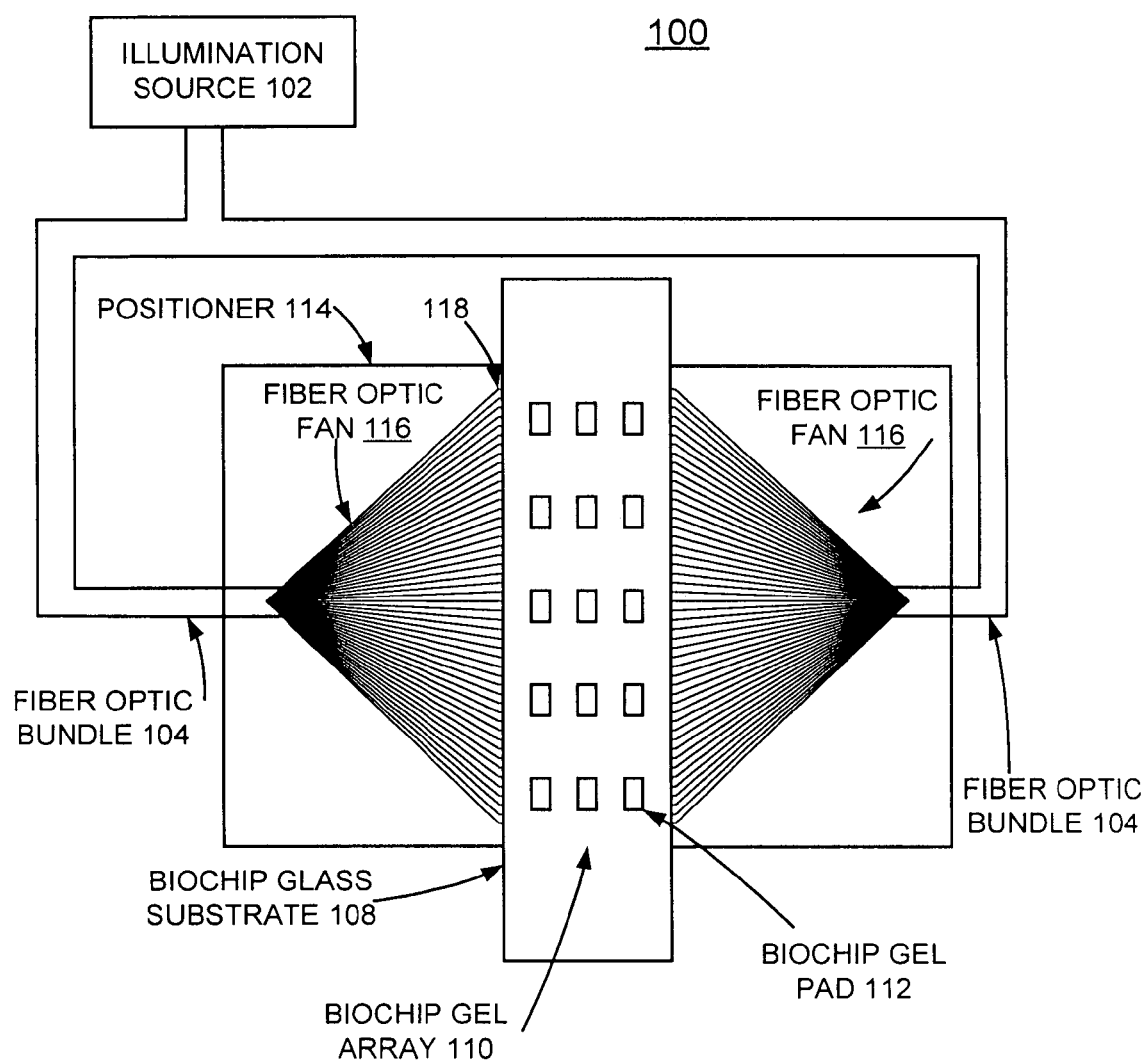
FIG. 1A is a schematic diagram representation illustrating biochip illumination apparatus for implementing the novel biochip method of illumination in accordance with the preferred embodiment.

Having reference now to the drawings, FIG. 1 illustrates biochip illumination apparatus generally designated by the reference character 100 for implementing the novel biochip method of illumination in accordance with the preferred embodiment. Biochip illumination apparatus includes an illumination source 102.

Illumination is provided, for example, by a low power (3-5 mW) non-collimated laser diode 102 emitting at specific wavelength such as, between 470 nm and 650 nm. Alternatively, a light emitting diode (LED) coupled with optical filter can also be used as an illumination source 102. As an optical filter, standard filters can be used, for example: bandpass filters, longpass or shortpass barrier filters, and rejection band filters. For example, the following LED from the Newark catalog provides intensity equivalent to 5-10 mW: Super bright LED, green, 150 mcd, 50 deg, http://www.newark.com. An explanation how to translate milicandela units to miliwatts can be found in the Basic Radiometry manual, http://www.opsci.com/technical.

As shown in FIG. 1A, a pair of fiber optic bundles 104 directs the light to opposing sides of a glass substrate 108. The glass substrate or slide 108 supports a biochip gel array or bioarray 110 including a plurality of biochip gel pads 112. The light is directed to the opposing sides of the glass substrate 108 by the fiber optic bundles 104 that are, for example, formed by borosilicate fiber light guides, quartz fiber light guides or plastic fiber light guides or fiber light guides formed by another suitable material.

Figure 1B:
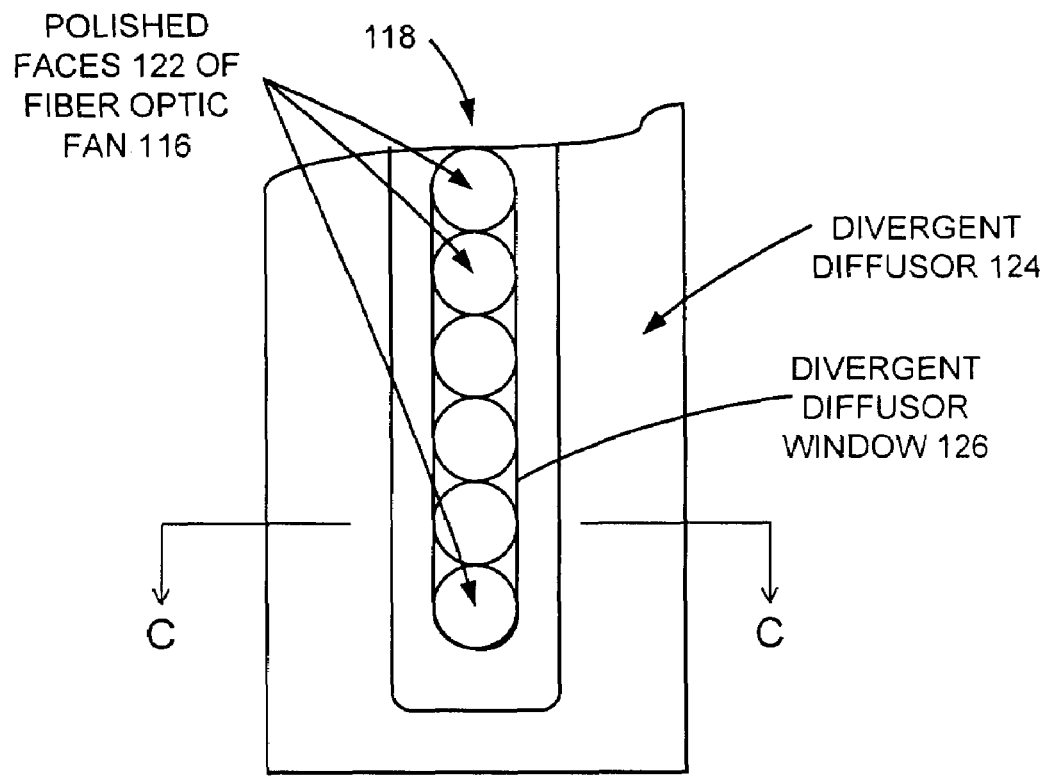
FIGS. 1B, 1C, 1D, and 1E are detailed schematic diagram representations illustrating portions of the biochip illumination apparatus of FIG. 1A.
Figure 1C:
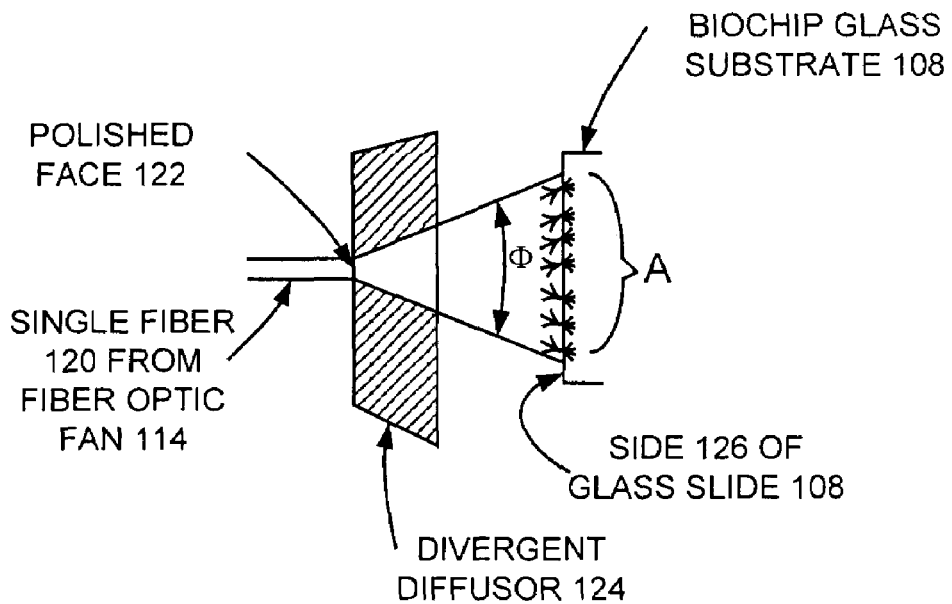

Referring now to FIGS. 1A, 1B and 1C, the fiber optic bundles 104 are carried by a positioner 114 and are splayed out to make a respective fiber optic fan generally designated by the reference character 116. The fiber optic fans 116 are one fiber thick, each defining a light line 118 or linear array of a plurality of optical fibers 120. Each of the fiber optic bundles 104 includes a plurality of optical fibers 120 providing generally symmetrical illumination to the opposing sides of the glass substrate 108. A single fiber 120 is illustrated in FIG. 1C that is taken along line C-C of FIG. 1B. Each optical fiber 120 includes a polished face 122 positioned proximate to a divergent diffuser 124. The optical fiber fans 116 define the light line 118 of the plurality of optical fiber ends or faces 122 of the respective optical fibers 120 that are received within a window 126 of the divergent diffuser 124.

The polished optical fiber faces 122 defining the light line 118 transfer laser light to opposing sides 126 of the glass substrate 108 via the divergent diffuser 124 with only a small percentage of the laser light going back into the optical fiber 120. This illumination process of the preferred embodiment randomizes any non-uniformity in the laser source 102, creating a more uniform illumination source.

A thin line of light is coupled by the respective divergent diffusers 124 to illuminate the reacted bioarray 110 through a respective edge or sidewall 126 of the glass substrate 108 which diffuse light evenly and the bioarray is illuminated from the inside of the glass substrate 108. The glass substrate 108 functions as a secondary light guide. The sidewalls 126 of the glass substrate 108 diffuse light and are not polished. Typically, commercially available glass substrate or slides 108 are not polished and do not require any additional treatment to diffuse light. The divergent diffuser 124 provides mechanical protection for the polished faces 122 of the optical fibers 120. The divergent diffuser 124 reflects back outwardly going light to the glass 108 to increase illumination efficiency.

As shown in FIG. 1C, each optical fiber face 122 couples light through the divergent diffuser 124 at a restricted angle labeled Φ. The divergent diffuser 124 is formed of a silicon material. The divergent diffuser 124 is spaced apart from the sidewall 126 of the glass substrate 108, for example, by 600 microns. The restricted angle Φ of light transfer is for example, 55° to 60°. Multiple arrows labeled A indicate light diffusion or mixing from each optical fiber face 122 coupled to the edge 126 of the glass substrate 108.

Figure 1D:
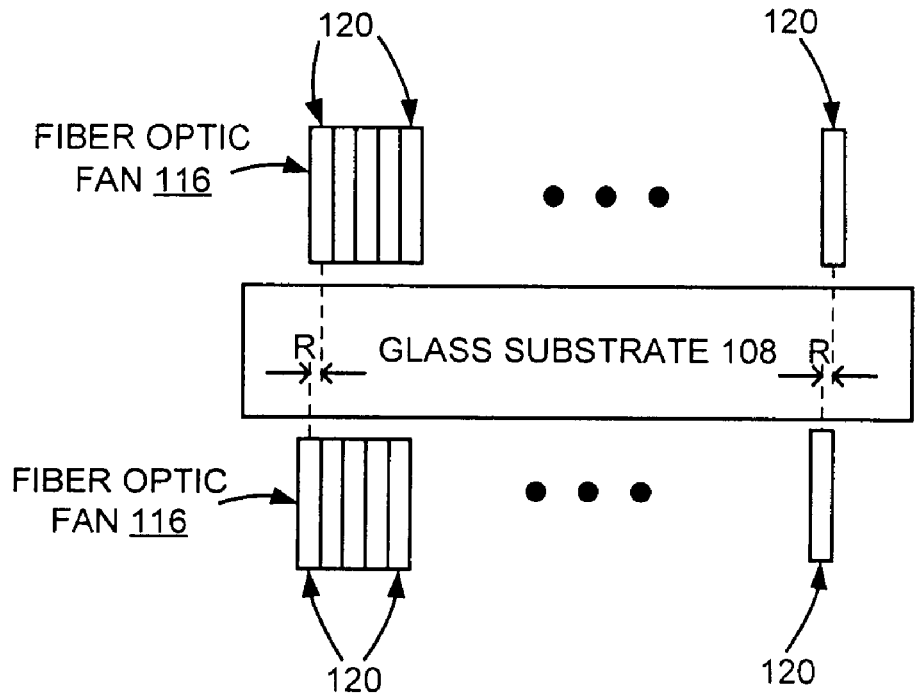

Referring now to FIG. 1D, opposite fiber optic fans 116 are shown with the glass substrate 108. As indicated by arrows labeled R, the respective centers of sequential fibers 120 of the opposite fiber optic fans 116 are offset or shifted by one radius size. This offset arrangement of the opposite fiber optic fans 116 improves light distribution within the glass substrate 108.

Figure 1E:
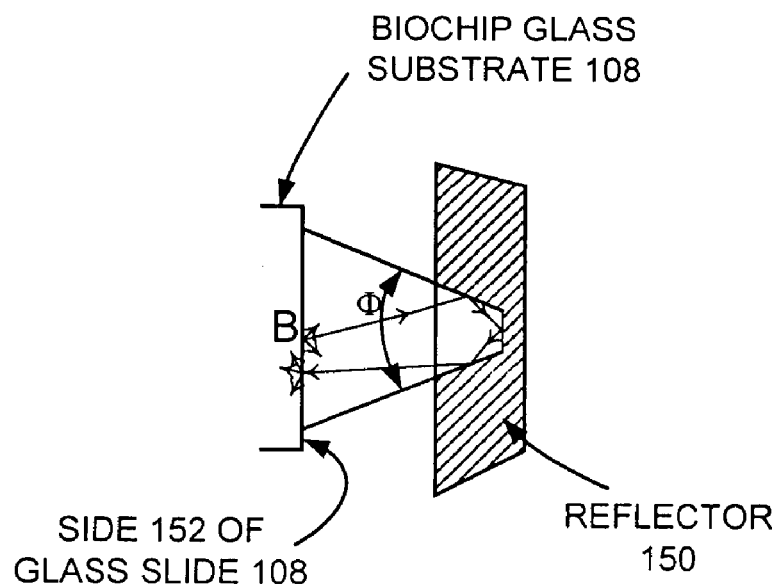

Referring now to FIG. 1E, a reflector 150 can be provided to reflect outwardly going light back to the glass substrate 108 and thus avoid loss of light during illumination. One or more reflectors 150 can be provided proximate to one or more respective ends 152 or endwalls of the glass substrate 108 that are spaced apart and separate from the divergent diffusers 124 or fiber optic fans 116. For example, the reflector 150 can be similar to the divergent diffuser 124 having generally the same restricted angle Φ of light reflection but without the open window 126.

FIGS. 2A, 2B, 2C, 2D, and 2E illustrate alternative biochip illumination arrangements in accordance with the preferred embodiment. The same reference numbers as used with illumination apparatus 100 of FIGS. 1A and 1B are used for similar or identical components in FIGS. 2A, 2B, 2C, 2D, and 2E. As shown in FIGS. 2A, 2B, 2C, 2D, and 2E, the present invention is not limited to the use of a single pair of optical fiber bundles 116 to direct the light into opposing sides of the glass substrate 108. A second pair of optical fiber bundle fans 116 can be provided to direct the light into opposing ends of the glass substrate 108; or a single optical fiber bundle fan 116 or three optical fiber bundles 116 can be provided to direct the light into the glass substrate 108. The number of optical fiber bundle fans 116 provided depends on the size of an area of the glass substrate 108 that needs to be illuminated. In general, the entire perimeter of the glass substrate 108 including both opposing sides and both opposing ends, advantageously can be illuminated to obtain maximum uniformity.

Figure 2A:
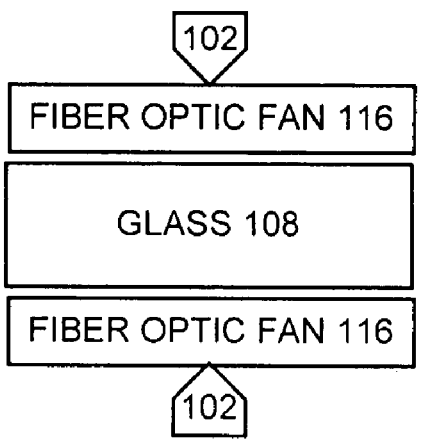
FIGS. 2A, 2B, 2C, 2D, and 2E are schematic diagram representations illustrating alternative biochip illumination arrangements in accordance with the preferred embodiment.

Referring to FIG. 2A, there is shown illumination apparatus generally designated by the reference character 200 for implementing the novel biochip method of illumination in accordance with the preferred embodiment. Illumination apparatus 200 includes a pair of fiber optic fans 116 on opposing sides of glass substrate 108 with a respective light source 102 coupled to each fiber optic fan 116.

Figure 2B:
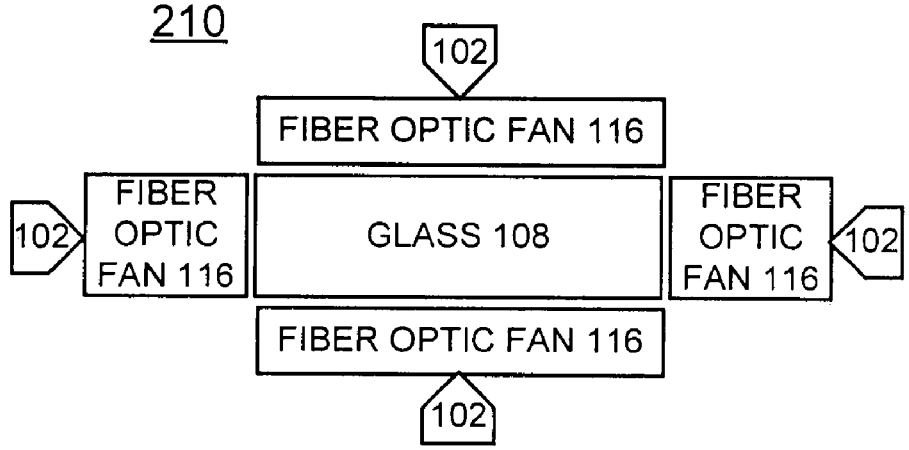

Referring to FIG. 2B, there is shown illumination apparatus generally designated by the reference character 210 for implementing the novel biochip method of illumination in accordance with the preferred embodiment. Illumination apparatus 210 includes a first pair of fiber optic fans 116 on opposing sides of glass substrate 108 and a second pair of fiber optic fans 116 on opposing ends of glass substrate 108 with a respective light source 102 coupled to each fiber optic fan 116.

Figure 2C:
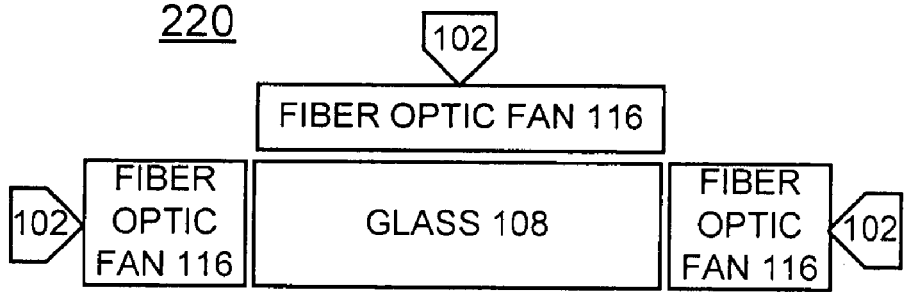

Referring to FIG. 2C, there is shown illumination apparatus generally designated by the reference character 220 for implementing the novel biochip method of illumination in accordance with the preferred embodiment. Illumination apparatus 220 includes a pair of fiber optic fans 116 on opposing ends of glass substrate 108 and a fiber optic fan 116 on one side of glass substrate 108 with a respective light source 102 coupled to each fiber optic fan 116.

Figure 2D:
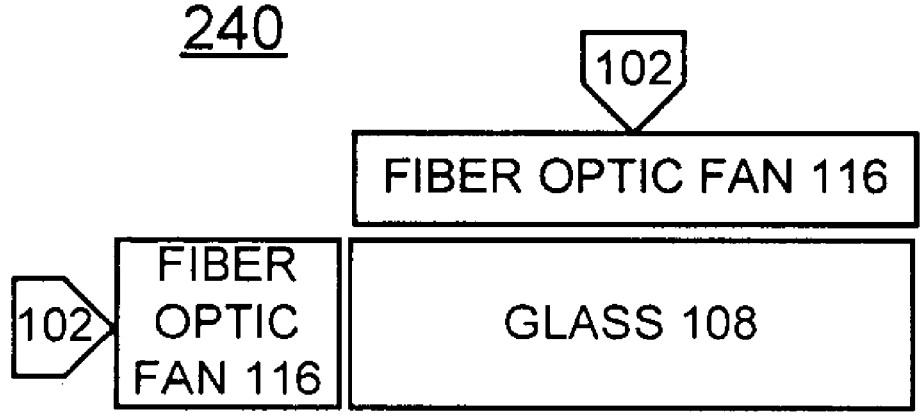

Referring to FIG. 2D, there is shown illumination apparatus generally designated by the reference character 240 for implementing the novel biochip method of illumination in accordance with the preferred embodiment. Illumination apparatus 240 includes a first fiber optic fan 116 on one side of glass substrate 108 and a second fiber optic fan 116 on one end of glass substrate 108 with a respective light source 102 coupled to each fiber optic fan 116.

Figure 2E:
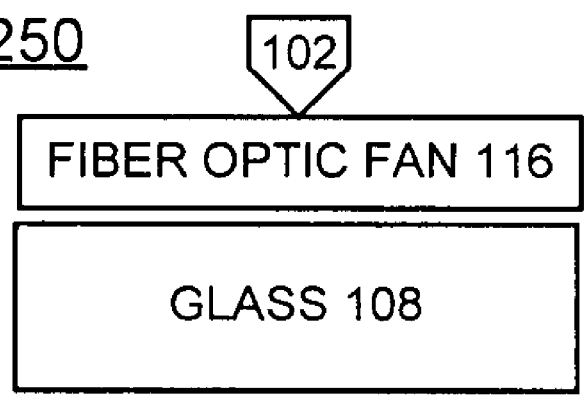

Referring to FIG. 2E, there is shown illumination apparatus generally designated by the reference character 250 for implementing the novel biochip method of illumination in accordance with the preferred embodiment. Illumination apparatus 250 includes a single fiber optic fan 116 on one side of glass substrate 108 with a light source 102 coupled to the fiber optic fan 116.

It should be understood that in each illumination apparatus 100, 200, 210, 220, 240, and 250, various low power lasers or light emitting diodes (LEDs) can be used for as the illumination source 102. Lasers 102 having different wavelength can be used in illumination apparatus 200, 210, 220, and 240. The different wavelength lasers 102 can be used sequentially depending upon a particular target's label.

Referring now to FIGS. 3, 4 and 5, there is shown a glass holder generally designated by the reference character 300 in accordance with the preferred embodiment for precisely positioning the glass 108 supporting multiple biochip gel arrays. Glass holder 300 includes a support housing 302 including opposing sidewalls 304, 306 and opposing front and rear walls 308, 310. Glass holder includes a glass-receiving cavity 312 including a bottom surface 314 carrying a rectangular plastic springs member 316. A Pressure sensitive fastener or VELCR® brand fastener material advantageously forms the plastic springs member 316. The glass 108 sits on the plastic springs member 316 with low contact force. A pair of spring loaded rollers 320, 322 and an axis member 324 are mounted within an upper surface 326 of the glass holder support housing 302 engaging the glass 108 with a low contact force. The glass 108 supporting the biochip gel array is easily inserted into and removed from the glass-receiving cavity 312 carried by the plastic springs member 316. The plastic springs member 316 pushes up on the glass 108 providing an effective focal plane for reading a particular biochip gel array carried by the glass 108. Glass holder 300 can be used with the bioarray carried by the glass substrate 108 when covered or not covered with a reaction chamber and the bioarray is provided in the focal plane of an optical system.

In accordance with features of the invention, this method of illumination provides a significantly improved illumination of the biochip gel pads 112 within the biochip array 110. This method of illumination provides a superior signal to noise ratio as compared with conventional illumination systems.

Two variants of bioarray illumination were modeled and tested for comparison of the illumination of the invention with conventional biochip illumination. The first variant of bioarray illumination uses conventional biochip illumination where the light beams from laser hit the bioarray directly from above the biochip array. The second uses the illumination apparatus 100 of the preferred embodiment including an intermediate fiber light guide (touch-to-line) which transmits light through diffuser 122 and the side 126 of the glass substrate 108 into the glass substrate, so that the light illuminates the bioarray 110 from inside of the glass substrate. The glass substrate 108 is used as the secondary light guide in accordance with the preferred embodiment.

For both types of illumination, the uniformity was measured using fluorescent signal from empty glass. Two images was acquired: with exposure time equal to 3 seconds for the first scheme and with exposure time equal to 20 seconds for the second scheme. The exposure times were selected so that the fluorescent intensities are generally of the same order. Additional acquisition was taken for each scheme without illumination with the same exposure time to subtract the dark current of a charge coupled device (CCD) camera.

The following tables A and B contain average fluorescent signal respectively collected from small areas of image arranged into grid using conventional illumination and with illumination apparatus 100 of the preferred embodiment. The value is calculated as the sum of pixel intensities divided by the square of the area.

(For the first scheme conventional light from above the biochip array, 3 seconds, dark current subtraction):

TABLE A

| with conventional illumination apparatus | | | | | | | | | | |
|---|---|---|---|---|---|---|---|---|---|---|
| 8.406 | 8.722 | 8.958 | 8.917 | 9.06 | 9.152 | 8.679 | 8.241 | 7.651 | 7.096 | 6.661 |
| 9.982 | 12.75 | 11.91 | 12.038 | 11.283 | 12.452 | 12.008 | 10.429 | 9.749 | 10.752 | 7.822 |
| 11.365 | 12.925 | 13.325 | 14.794 | 13.584 | 14.366 | 14.071 | 12.755 | 12.285 | 11.35 | 9.785 |
| 12.665 | 14.39 | 14.454 | 14.865 | 16.615 | 15.393 | 14.814 | 14.234 | 13.722 | 15.4 | 10.668 |
| 13.706 | 15.273 | 16.175 | 17.614 | 16.928 | 17.232 | 16.138 | 15.468 | 17.111 | 15.264 | 11.693 |
| 14.429 | 16.654 | 17.268 | 18.605 | 17.651 | 16.716 | 15.824 | 16.161 | 15.572 | 14.222 | 11.751 |
| 14.338 | 16.796 | 17.336 | 19.784 | 16.818 | 15.992 | 15.019 | 15.012 | 14.484 | 13.326 | 11.247 |
| 13.254 | 15.569 | 16.563 | 17.343 | 15.858 | 15.185 | 14.402 | 14.591 | 13.589 | 12.711 | 10.725 |

TABLE A-continued with conventional illumination apparatus

| | | | | | | | | | | |
|---|---|---|---|---|---|---|---|---|---|---|
| 11.083 | 12.71 | 13.159 | 14.05 | 13.404 | 12.079 | 11.848 | 11.86 | 10.863 | 11.196 | 8.951 |
| 9.542 | 9.434 | 10.572 | 10.921 | 10.221 | 10.063 | 9.276 | 8.938 | 8.693 | 8.056 | 7.306 |

(For the second illumination scheme in accordance with the preferred embodiment with illumination light from sides, 20 seconds, dark current subtraction):

TABLE B with illumination apparatus 100

| | | | | | | | | | | |
|---|---|---|---|---|---|---|---|---|---|---|
| 5.416 | 6.339 | 6.462 | 6.941 | 6.96 | 6.97 | 7.213 | 6.978 | 7.128 | 7.238 | 6.881 |
| 5.502 | 7.246 | 6.923 | 7.487 | 7.107 | 7.879 | 7.595 | 7.199 | 7.324 | 9.082 | 7.048 |
| 6.158 | 7.021 | 6.969 | 7.455 | 7.353 | 7.331 | 7.469 | 7.302 | 7.479 | 7.406 | 7.094 |
| 6.515 | 7.44 | 7.065 | 7.066 | 7.382 | 7.145 | 7.236 | 7.411 | 7.534 | 8.124 | 7.352 |
| 6.523 | 7.475 | 7.208 | 7.53 | 7.242 | 7.494 | 7.463 | 7.474 | 7.797 | 7.953 | 6.847 |
| 7.103 | 7.755 | 7.678 | 7.815 | 7.547 | 7.48 | 7.182 | 7.335 | 7.458 | 7.375 | 6.982 |
| 7.18 | 7.947 | 7.579 | 8.073 | 7.451 | 7.276 | 7.175 | 7.28 | 7.328 | 7.301 | 7.15 |
| 7.148 | 8.011 | 7.96 | 7.678 | 7.798 | 7.482 | 7.484 | 7.328 | 7.102 | 7.178 | 6.902 |
| 7.498 | 7.792 | 7.967 | 8.112 | 7.654 | 7.216 | 7.09 | 7.384 | 7.382 | 7.216 | 6.903 |
| 6.945 | 7.694 | 7.593 | 7.383 | 7.405 | 7.445 | 7.602 | 7.585 | 7.041 | 6.909 | 6.833 |

The purpose of biochip reader is to measure fluorescent signals acquired from different pads of a microarray. Unevenness of illumination is one of the major sources of error in measurements. When the fluorescent signals are greater enough than the noise of CCD camera, the non-uniformity of illumination is the only source of error in such measurements.

Consider the relative standard deviation (RSD), defined as the standard deviation divided by the average value, is a measure of the uniformity of illumination. The RSD is the simplest criteria that reflect the quality of illumination. The uniformity of illumination is better and the error is less when the RSD is less.

| | Average value | Standard deviation | RSD |
|---|---|---|---|
| First scheme | 12.92877 | 3.005968 | 0.23 |
| Second scheme | 7.303645 | 0.471795 | 0.064 |

On basis of data analysis the second scheme of illumination with illumination apparatus 100 of the preferred embodiment provides 3.6 times better uniformity and correspondingly 3.6 times less error than the first conventional illumination scheme.

Figure 6:
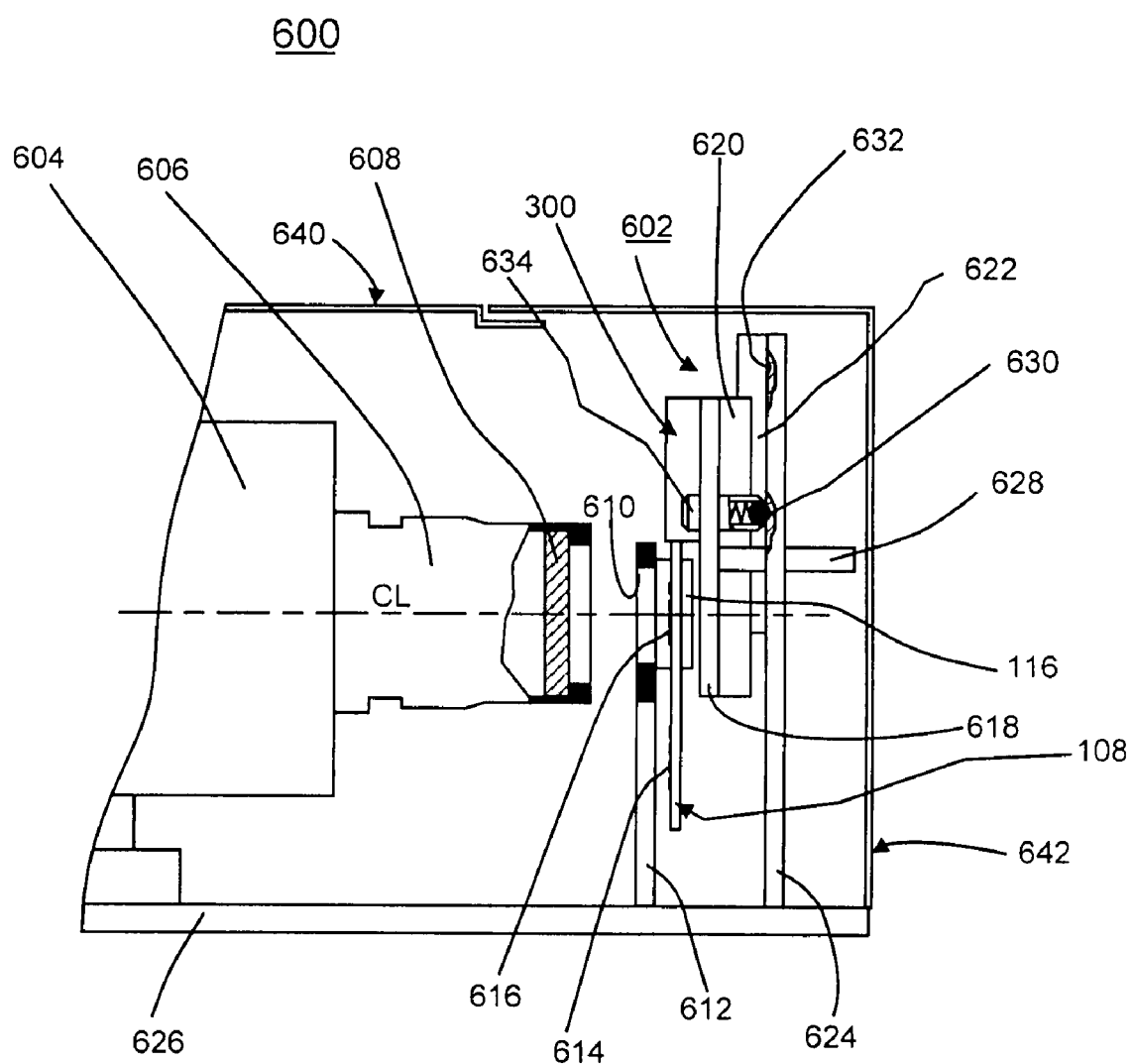
FIG. 6 illustrates a biochip reader including glass holder of FIG. 3 together with a positioner used with the biochip illumination apparatus in accordance with the preferred embodiment.

Referring to FIG. 6, a biochip reader generally designated by the reference character 600 includes biochip illumination apparatus 100, the glass holder 300 together with a manual positioner generally designated by the reference character 602 in accordance with the preferred embodiment. Biochip reader 600 is generally inexpensive, portable, lightweight, and simple to implement. Biochip reader 600 is illustrated in simplified form sufficient for understanding the present invention.

Biochip reader 600 includes a charge coupled device (CCD) camera 604, a lens/lens array 606, and a filter 608. The CCD camera 604 and associated lens/lens array 606 and filter 608 are aligned with a window 610 in a first plate 612.

A centerline through the window 610 and the CCD camera 604 and associated lens/lens array 606 and filter 608 is labeled CL. In the biochip reader 600, the glass holder 300 includes the plastic springs member 316 as seen in FIG. 3 that pushes up on the glass 108 with low contact forces providing an effective focal plane for reading a particular one of two biochip gel arrays 614, 616 carried by the glass 108. A light guide, fiber optic fan 116 is disposed proximate to the glass substrate 108 generally aligned with the window 610. The manual positioner 602 includes a first ball bearing slide 620 coupled to a plate 618 and to the glass holder 300 and a second ball bearing slide 622 coupled to a stationary second plate 624. The manual positioner 602 includes a base plate 626 supporting plates 612 and 624. The manual positioner 602 includes a lever 628 extending through a slot (not shown) in the stationary second plate 624 and is mounted to the plate 618. A plunger pin 634 also is mounted to plate 618. A pair of stop points 630 and 632 is formed within the second plate 624 for engagement with the plunger pin 634 of the manual positioner 602. The lever 628 is manually moved, moving the ball bearing slide 620, plate 618, plunger pin 634, and the glass holder 300 and the glass substrate 108 carrying the two biochip gel arrays 614, 616.

As shown in FIG. 6, the plunger pin 634 is received within the stop point 630, the biochip gel array 616 is aligned with window 610 for reading. When the lever 628 of manual positioner 602 is slidingly moved to position the plunger pin 634 with the stop point 632, the biochip gel array 614 is aligned with window 610 for reading. Biochip reader 600 includes a case 640 and a hood 642 containing the manual positioner 602, glass holder 300, the CCD camera 604 and associated lens/lens array 606 and filter 608.

In order to evaluate the use of biochip reader 600 for registration of fluorescent signals from biochips manufactured with use of different commercially available glass slides, the following experiment was carried out. Biochips containing a set of probes were produced by using slides from Motorola (3D-Link), Telechem (Superaldehyde), and Packard Bioscience (Hydrogel), as indicated in the following Tables 1 and 2. After the application of oligonucleotides bearing 5'-end amino group, the immobilization was carried out according to procedures recommended by the manufacturers.

Hybridizations with a mix of Texas Red labeled target oligonucleotides (5 fmol/µl) (Table 3) were carried for 4 h at 25° C. in 200-µl hybridization chamber (Grace Biolabs). Hybridization buffer contained 1 M guanidine isothiocyanate, 50 mM HEPES (pH 7.5), and 10 mM EDTA. After hybridization the biochips were washed for 30 sec with 6×SSPE with 0.1% Triton X-100, washed for 5 sec with MilliQ water, and dried. Hybridization signals from the biochips were recorded on the biochip reader 600 and on a commercially available scanner, Model: Bio-Chip Imager, Part No.: 902-3013001 manufactured by Packard Instrument Company, Inc., now it is Packard Bioscience.

The fluorescence intensities data was analyzed using two methods. First, the correlation function was calculated for all biochip elements of 4 chips located on slide, separately for different slide types. The correlation function is defined, for $X[i]$ and $Y[i]$, as $M((x-Mx)(y-My))/(MxMy)$, where M is average of its argument array. The feature of the correlation function is that it equals 1 when and only when X and Y arrays are congruent. Since the signal is proportional to the amount of fluorescent substance, the correlation in readings between the biochip reader 600 and the scanner shows the ability of the biochip reader 600 to acquire these signals.

In the second calculation, 4 groups of biochip elements are considered: bare glass, probes that do not hybridize, probes that show hybridization with labeled target, and biochip elements with pre-immobilized labeled oligonucleotides used as markers. Correlation of average signals from all 4 types of biochip elements is also calculated for all slide types.

Table 4 summarizes data for correlation between fluorescent signals recorded by the biochip reader 600 and the scanner. For all biochips the correlation between fluorescent intensities acquired by the biochip reader 600 and the scanner is positive, and is greater than 0.9 when calculated for different types of biochip elements. This data shows the applicability of the biochip reader 600 for measurement of fluorescent signals from commercially available biochips and biochips manufactured with use of different commercially available glass slides.

TABLE 1

Scheme for probe location for the biochip

| 1004 | 1005 |    |    |    |    |    |    |    | 1004 | 1005 |
|------|------|----|----|----|----|----|----|----|------|------|
|      |      | 1  | 11 | 21 | 31 | 41 | 51 |    |      |      |
|      |      | 2  | 12 | 22 | 32 | 42 |    |    |      |      |
|      | 52   | 3  | 13 | 23 | 33 | 43 |    | 52 |      |      |
|      |      | 4  | 14 | 24 | 34 | 44 |    |    |      |      |
|      | 52   | 5  | 15 | 25 | 35 | 45 |    | 52 |      |      |
|      |      | 6  | 16 | 26 | 36 | 46 |    |    |      |      |
|      | 52   | 7  | 17 | 27 | 37 | 47 |    | 52 |      |      |
|      |      | 8  | 18 | 28 | 38 | 48 |    |    |      |      |
|      |      | 9  | 19 | 29 | 39 | 49 |    |    |      |      |
|      | 52   | 10 | 20 | 30 | 40 | 50 |    | 52 |      |      |
|      |      | 1  | 11 | 21 | 31 | 41 | 51 |    |      |      |
|      |      | 2  | 12 | 22 | 32 | 42 |    |    |      |      |
|      | 52   | 3  | 13 | 23 | 33 | 43 |    | 52 |      |      |
|      |      | 4  | 14 | 24 | 34 | 44 |    |    |      |      |
|      | 52   | 5  | 15 | 25 | 35 | 45 |    | 52 |      |      |
|      |      | 6  | 16 | 26 | 36 | 46 |    |    |      |      |
|      | 52   | 7  | 17 | 27 | 37 | 47 |    | 52 |      |      |
|      |      | 8  | 18 | 28 | 38 | 48 |    |    |      |      |
|      |      | 9  | 19 | 29 | 39 | 49 |    |    |      |      |
|      | 52   | 10 | 20 | 30 | 40 | 50 |    | 52 |      |      |
|      |      |    |    |    |    |    |    |    | 1004 | 1005 |

TABLE 2

List of oligonucleotide probes used for biochip manufacturing

| Solution # | Contents (Sequence) | C, mM |
|---|---|---|
| 1 | CTTTRGAAAATAIGAGATAATT | 1 |
| 2 | TTGAGTAAATAGGRTATAATTG | 1 |
| 3 | TTGAGTARATAAGATATAACTG | 1 |
| 4 | TTACCCGATTCCRGGTTAATT | 1 |
| 5 | TTACCCGATTCTRGGTTAATT | 1 |
| 6 | GAGGRTAYACGAATTACTAC | 1 |
| 7 | GTATTTCCGCATTGTGAYGC | 1 |
| 8 | GTATTTTCGCATTGAGAYGC | 1 |
| 9 | TATACGTTCGTGTGCAGT | 1 |
| 10 | GTAAATCTGTTCTATGCTGT | 1 |
| 11 | CTTAARAAAACGAGTGATAATT | 1 |
| 12 | YCTGTTACAGTGTTTAATAGTTT | 1 |
| 13 | AAACTTGYCAAAGCTGTYAGA | 1 |
| 14 | TTGATAATTRCATTACGGCTA | 1 |
| 15 | TTGATAATCACATTRCGGCTA | 1 |
| 16 | TAATIAYGAGACTTCTCCAGT | 1 |
| 17 | TTTTACGATTGCCTTTYTGGATA | 1 |
| 18 | GTTATAATGATTGTAGTATCC | 1 |
| 19 | TTGAATTGAATARTTCGTAGT | 1 |
| 20 | GTTATAATGATTGTAGTATCC | 1 |
| 21 | TTGAATTGAATARTTCGTAGT | 1 |
| 22 | AAATGCTAAGCATGAATATGG | 1 |
| 23 | AGATGCTAAGCAYGAGTATGG | 1 |
| 24 | AGTCITGATAATAYTTGGAYGTA | 1 |
| 25 | TTTCTAATACATSGGTIAATTTGAG | 1 |
| 26 | ATAGGCAATGGGRCTGATA | 1 |
| 27 | GITTATTTGCAGTTAARGGG | 1 |
| 28 | GTTTATTCGCAGTTAARGGG | 1 |
| 29 | CACTGTTGTAGCAAATAGG | 1 |
| 30 | TCGTTTAGAGGTGACGTCYT | 1 |
| 31 | RCATAAATATAAACATAGTGTG | 1 |
| 32 | ACCTAAAATCACGCAAAGGATATCAA | 1 |
| 33 | ATYGATATTRCATCRTTAACAAG | 1 |
| 34 | AAAYCATCTGAYTAATTATTCTATA | 1 |
| 35 | TCACAATAATTTAAAATGCTCT | 1 |
| 36 | GTCGTCAATAGCATTAATAATAC | 1 |
| 37 | GTAGCCAATAGCGTTAATAATA | 1 |
| 38 | GATGCTAATGATATATTTCCATA | 1 |
| 39 | ACRTTCTATTGTGAAGGTGCYTC | 1 |
| 40 | ATATTTCAAGCYCCATAGTAG | 1 |
| 41 | GAGTGCCCTAATCCAGTG | 1 |
| 42 | CTGTGTTCTTAGGTATTATG | 1 |
| 43 | ATTGCTTACGGAGGTGATTTTG | 1 |
| 44 | ATCATTTCCATGTAGAGTTGC | 1 |
| 45 | TCTTYTGCACCCTARTCYATTTGA | 1 |
| 46 | GTYCAATTCTACCTTCTATGA | 1 |
| 47 | GACTTGRAGAGGTACRTTTTC | 1 |
| 48 | GACTTGGAGAAGTACATTTTC | 1 |
| 49 | GCATTRCTTCTCTGAATGAAT | 1 |
| 50 | AGTTAGTTGTAATCCACTATAC | 1 |
| 51 | ATTTTGCGATCAATATACACAT | 1 |
| 52 | GAT GAT GAT GAT GAT GAT GA | 2 |
| 1004 | TR-TTTTTTTT-NH2 | 0.1 |
| 1005 | TMR-TTTTTTTT-NH2 | 0.1 |
|  | Sequences Listed from 5' to 3' | |
|  | All oligos contain 5' C6 NH2 | |
|  | IUPAC Nucleotide designations | |
|  | M A/C | |
|  | R A/G | |
|  | Y C/T | |
|  | W A/T | |
|  | S C/G | |
|  | K G/T | |
|  | V A/G/C | |
|  | H A/C/T | |
|  | D A/G/T | |
|  | B C/G/T | |
|  | N A/G/C/T | |
|  | I Inosine | |

TABLE 3

Sequences of target oligonucleotides and complimentary probes and probe numbers

| Sequence of target (5' -> 3') | Sequence of complementary probe (5' -> 3') | Number of probe on a biochip |
|---|---|---|
| CAATTATAYCCTATTTACTCAA | TTGAGTAAATAGGRTATAATTG | 2 |
| T(5)-AATTAACCYAGAATCGGGTAA-T(5) | TTACCCGATTCTRGGTTAATT | 5 |
| T(15)-TCTRACAGCTTTGRCAAGTTT-T(15) | AAACTTGYCAAAGCTGTYAGA | 13 |
| TATCAGYCCCATTGCCTAT | ATAGGCAATGGGRCTGATA | 26 |
| CCCYTTAACTGCGAATAAAC | GTTTATTCGCAGTTAARGGG | 28 |
| T(20)-CCTATTTGCTACAACAGTG-T(20) | CACTGTTGTAGCAAATAGG | 29 |
| ARGACGTCACCTCTAAACGA | TCGTTTAGAGGTGACGTCYT | 30 |
| CTTGTTAAYGATGYAATATCRAT | ATYGATATTRCATCRTTAACAAG | 33 |
| T(10)-TCAAATRGAYTAGGGTGCARAAGA-T(10) | TCTTYTGCACCCTARTCYATTTGA | 45 |
| GTATAGTGGATTACAACTAACT | AGTTAGTTGTAATCCACTATAC | 50 |
| CAATTATAYCCTATTTACTCAA | GATGATGATGATGATGATGA | 52 |

TABLE 4

Correlation for biochips acquired by Reader and scanner

| Slide Manufacturer | Correlation for all elements | Correlation for groups |
|---|---|---|
| Motorola | 0.87 | 0.99 |
| Packard | 0.81 | 0.92 |
| Telechem | 0.61 | 0.99 |

While the present invention has been described with reference to the details of the embodiments of the invention shown in the drawing, these details are not intended to limit the scope of the invention as claimed in the appended claims.

What is claimed is:

1. A biochip reader comprising:
   an illumination source,
   a glass substrate carrying a bioarray;
   an optical fiber bundle directing said light from said illumination source to one side of said glass substrate; said optical fiber bundle including a plurality of optical fibers;
   a reflector positioned proximate to another side of said glass substrate spaced apart from said fiber optic fan; said reflector for reflecting outgoing light back into said glass substrate
   an optical system;
   a glass holder supporting and aligning said glass substrate carrying the bioarray with said optical system, and
   said glass holder including a plastic springs member in contact engagement with said glass substrate with low contact forces for positioning said bioarray in a focal plane of said optical system.

2. A biochip reader as recited in claim 1 includes a positioner coupled to said glass holder for positioning said bioarray within a field of view of said optical system.

3. A biochip reader as recited in claim 1 includes an optical fiber fan formed by said optical fiber bundle proximate to a side of said glass substrate carrying said bioarray, said optical fiber fan defining a line of optical fiber faces of said plurality of optical fibers.

4. A biochip reader as recited in claim 3 includes a divergent diffuser separating said optical fiber faces from an edge of said glass substrate, said divergent diffuser protecting said optical fibers from mechanical damage.

5. A biochip reader as recited in claim 1 wherein said plastic springs member is formed of a pressure sensitive fastener material.

* * * * *

SEQUENCE LISTING

<160> NUMBER OF SEQ ID NOS: 74

<210> SEQ ID NO 1
<211> LENGTH: 22
<212> TYPE: DNA
<213> ORGANISM: Artificial
<220> FEATURE:
<223> OTHER INFORMATION: Completely Synthesized
<220> FEATURE:
<221> NAME/KEY: misc_feature
<222> LOCATION: (13)..(13)
<223> OTHER INFORMATION: modified base
<220> FEATURE:
<221> NAME/KEY: modified_base
<222> LOCATION: (13)..(13)
<223> OTHER INFORMATION: I

<400> SEQUENCE: 1
ctttrgaaaa tangagataa tt                                              22

<210> SEQ ID NO 2
<211> LENGTH: 22
<212> TYPE: DNA
<213> ORGANISM: Artificial
<220> FEATURE:
<223> OTHER INFORMATION: Completely Synthesized

<400> SEQUENCE: 2

```
ttgagtaaat aggrtataat tg                                              22

<210> SEQ ID NO 3
<211> LENGTH: 22
<212> TYPE: DNA
<213> ORGANISM: Artificial
<220> FEATURE:
<223> OTHER INFORMATION: Completely Synthesized

<400> SEQUENCE: 3
ttgagtarat aagatataac tg                                              22

<210> SEQ ID NO 4
<211> LENGTH: 21
<212> TYPE: DNA
<213> ORGANISM: Artificial
<220> FEATURE:
<223> OTHER INFORMATION: Completely Synthesized

<400> SEQUENCE: 4
ttacccgatt ccrggttaat t                                               21

<210> SEQ ID NO 5
<211> LENGTH: 21
<212> TYPE: DNA
<213> ORGANISM: Artificial
<220> FEATURE:
<223> OTHER INFORMATION: Completely Synthesized

<400> SEQUENCE: 5
ttacccgatt ctrggttaat t                                               21

<210> SEQ ID NO 6
<211> LENGTH: 20
<212> TYPE: DNA
<213> ORGANISM: Artificial
<220> FEATURE:
<223> OTHER INFORMATION: Completely Synthesized

<400> SEQUENCE: 6
gaggrtayac gaattactac                                                 20

<210> SEQ ID NO 7
<211> LENGTH: 20
<212> TYPE: DNA
<213> ORGANISM: Artificial
<220> FEATURE:
<223> OTHER INFORMATION: Completely Synthesized

<400> SEQUENCE: 7
gtatttccgc attgtgaygc                                                 20

<210> SEQ ID NO 8
<211> LENGTH: 20
<212> TYPE: DNA
<213> ORGANISM: Artificial
<220> FEATURE:
<223> OTHER INFORMATION: Completely Synthesized

<400> SEQUENCE: 8
gtattttcgc attgagaygc                                                 20

<210> SEQ ID NO 9
<211> LENGTH: 18
<212> TYPE: DNA
```

```
<213> ORGANISM: Artificial
<220> FEATURE:
<223> OTHER INFORMATION: Completely Synthesized

<400> SEQUENCE: 9
tatacgttcg tgtgcagt                                                  18

<210> SEQ ID NO 10
<211> LENGTH: 20
<212> TYPE: DNA
<213> ORGANISM: Artificial
<220> FEATURE:
<223> OTHER INFORMATION: Completely Synthesized

<400> SEQUENCE: 10
gtaaatctgt tctatgctgt                                                20

<210> SEQ ID NO 11
<211> LENGTH: 22
<212> TYPE: DNA
<213> ORGANISM: Artificial
<220> FEATURE:
<223> OTHER INFORMATION: Completely Synthesized

<400> SEQUENCE: 11
cttaaraaaa cgagtgataa tt                                             22

<210> SEQ ID NO 12
<211> LENGTH: 23
<212> TYPE: DNA
<213> ORGANISM: Artificial
<220> FEATURE:
<223> OTHER INFORMATION: Completely Synthesized

<400> SEQUENCE: 12
yctgttacag tgtttaatag ttt                                            23

<210> SEQ ID NO 13
<211> LENGTH: 21
<212> TYPE: DNA
<213> ORGANISM: Artificial
<220> FEATURE:
<223> OTHER INFORMATION: Completely Synthesized

<400> SEQUENCE: 13
aaacttgyca aagctgtyag a                                              21

<210> SEQ ID NO 14
<211> LENGTH: 21
<212> TYPE: DNA
<213> ORGANISM: Artificial
<220> FEATURE:
<223> OTHER INFORMATION: Completely Synthesized

<400> SEQUENCE: 14
ttgataattr cattacggct a                                              21

<210> SEQ ID NO 15
<211> LENGTH: 21
<212> TYPE: DNA
<213> ORGANISM: Artificial
<220> FEATURE:
<223> OTHER INFORMATION: Completely Synthesized

<400> SEQUENCE: 15
ttgataatca cattrcggct a                                              21
```

```
<210> SEQ ID NO 16
<211> LENGTH: 21
<212> TYPE: DNA
<213> ORGANISM: Artificial
<220> FEATURE:
<223> OTHER INFORMATION: Completely Synthesized
<220> FEATURE:
<221> NAME/KEY: misc_feature
<222> LOCATION: (5)..(5)
<223> OTHER INFORMATION: modified base
<220> FEATURE:
<221> NAME/KEY: modified_base
<222> LOCATION: (5)..(5)
<223> OTHER INFORMATION: I

<400> SEQUENCE: 16
taatnaygag acttctccag t                                           21

<210> SEQ ID NO 17
<211> LENGTH: 23
<212> TYPE: DNA
<213> ORGANISM: Artificial
<220> FEATURE:
<223> OTHER INFORMATION: Completely Synthesized

<400> SEQUENCE: 17
ttttacgatt gcctttytgg ata                                         23

<210> SEQ ID NO 18
<211> LENGTH: 21
<212> TYPE: DNA
<213> ORGANISM: Artificial
<220> FEATURE:
<223> OTHER INFORMATION: Completely Synthesized

<400> SEQUENCE: 18
gttataatga ttgtagtatc c                                           21

<210> SEQ ID NO 19
<211> LENGTH: 21
<212> TYPE: DNA
<213> ORGANISM: Artificial
<220> FEATURE:
<223> OTHER INFORMATION: Completely Synthesized

<400> SEQUENCE: 19
ttgaattgaa tarttcgtag t                                           21

<210> SEQ ID NO 20
<211> LENGTH: 21
<212> TYPE: DNA
<213> ORGANISM: Artificial
<220> FEATURE:
<223> OTHER INFORMATION: Completely Synthesized

<400> SEQUENCE: 20
gttataatga ttgtagtatc c                                           21

<210> SEQ ID NO 21
<211> LENGTH: 21
<212> TYPE: DNA
<213> ORGANISM: Artificial
<220> FEATURE:
<223> OTHER INFORMATION: Completely Synthesized

<400> SEQUENCE: 21
```
ttgaattgaa tarttcgtag t                          21

<210> SEQ ID NO 22
<211> LENGTH: 21
<212> TYPE: DNA
<213> ORGANISM: Artificial
<220> FEATURE:
<223> OTHER INFORMATION: Completely Synthesized

<400> SEQUENCE: 22
aaatgctaag catgaatatg g                          21

<210> SEQ ID NO 23
<211> LENGTH: 21
<212> TYPE: DNA
<213> ORGANISM: Artificial
<220> FEATURE:
<223> OTHER INFORMATION: Completely Synthesized

<400> SEQUENCE: 23
agatgctaag caygagtatg g                          21

<210> SEQ ID NO 24
<211> LENGTH: 23
<212> TYPE: DNA
<213> ORGANISM: Artificial
<220> FEATURE:
<223> OTHER INFORMATION: Completely Synthesized
<220> FEATURE:
<221> NAME/KEY: misc_feature
<222> LOCATION: (5)..(5)
<223> OTHER INFORMATION: modified base
<220> FEATURE:
<221> NAME/KEY: modified_base
<222> LOCATION: (5)..(5)
<223> OTHER INFORMATION: I

<400> SEQUENCE: 24
agtcntgata atayttggay gta                        23

<210> SEQ ID NO 25
<211> LENGTH: 25
<212> TYPE: DNA
<213> ORGANISM: Artificial
<220> FEATURE:
<223> OTHER INFORMATION: Completely Synthesized
<220> FEATURE:
<221> NAME/KEY: misc_feature
<222> LOCATION: (17)..(17)
<223> OTHER INFORMATION: modified base
<220> FEATURE:
<221> NAME/KEY: modified_base
<222> LOCATION: (17)..(17)
<223> OTHER INFORMATION: I

<400> SEQUENCE: 25
tttctaatac atsggtnaat ttgag                      25

<210> SEQ ID NO 26
<211> LENGTH: 19
<212> TYPE: DNA
<213> ORGANISM: Artificial
<220> FEATURE:
<223> OTHER INFORMATION: Completely Synthesized

<400> SEQUENCE: 26
ataggcaatg ggrctgata                             19

<210> SEQ ID NO 27
<211> LENGTH: 20
<212> TYPE: DNA
<213> ORGANISM: Artificial
<220> FEATURE:
<223> OTHER INFORMATION: Completely Synthesized
<220> FEATURE:
<221> NAME/KEY: misc_feature
<222> LOCATION: (2)..(2)
<223> OTHER INFORMATION: modified base
<220> FEATURE:
<221> NAME/KEY: modified_base
<222> LOCATION: (2)..(2)
<223> OTHER INFORMATION: I

<400> SEQUENCE: 27
gnttatttgc agttaargggg                                          20

<210> SEQ ID NO 28
<211> LENGTH: 20
<212> TYPE: DNA
<213> ORGANISM: Artificial
<220> FEATURE:
<223> OTHER INFORMATION: Completely Synthesized

<400> SEQUENCE: 28
gtttattcgc agttaargggg                                          20

<210> SEQ ID NO 29
<211> LENGTH: 19
<212> TYPE: DNA
<213> ORGANISM: Artificial
<220> FEATURE:
<223> OTHER INFORMATION: Completely Synthesized

<400> SEQUENCE: 29
cactgttgta gcaaatagg                                            19

<210> SEQ ID NO 30
<211> LENGTH: 20
<212> TYPE: DNA
<213> ORGANISM: Artificial
<220> FEATURE:
<223> OTHER INFORMATION: Completely Synthesized

<400> SEQUENCE: 30
tcgtttagag gtgacgtcyt                                           20

<210> SEQ ID NO 31
<211> LENGTH: 22
<212> TYPE: DNA
<213> ORGANISM: Artificial
<220> FEATURE:
<223> OTHER INFORMATION: Completely Synthesized

<400> SEQUENCE: 31
rcataaatat aaacatagtg tg                                        22

<210> SEQ ID NO 32
<211> LENGTH: 26
<212> TYPE: DNA
<213> ORGANISM: Artificial
<220> FEATURE:
<223> OTHER INFORMATION: Completely Synthesized

<400> SEQUENCE: 32
acctaaaatc acgcaaagga tatcaa                                    26

<210> SEQ ID NO 33
<211> LENGTH: 23
<212> TYPE: DNA
<213> ORGANISM: Artificial
<220> FEATURE:
<223> OTHER INFORMATION: Completely Synthesized

<400> SEQUENCE: 33
atygatattr catcrttaac aag                                              23

<210> SEQ ID NO 34
<211> LENGTH: 26
<212> TYPE: DNA
<213> ORGANISM: Artificial
<220> FEATURE:
<223> OTHER INFORMATION: Completely Synthesized

<400> SEQUENCE: 34
aaaaycatct gaytaattat tctata                                           26

<210> SEQ ID NO 35
<211> LENGTH: 22
<212> TYPE: DNA
<213> ORGANISM: Artificial
<220> FEATURE:
<223> OTHER INFORMATION: Completely Synthesized

<400> SEQUENCE: 35
tcacaataat ttaaaatgct ct                                               22

<210> SEQ ID NO 36
<211> LENGTH: 23
<212> TYPE: DNA
<213> ORGANISM: Artificial
<220> FEATURE:
<223> OTHER INFORMATION: Completely Synthesized

<400> SEQUENCE: 36
gtcgtcaata gcattaataa tac                                              23

<210> SEQ ID NO 37
<211> LENGTH: 22
<212> TYPE: DNA
<213> ORGANISM: Artificial
<220> FEATURE:
<223> OTHER INFORMATION: Completely Synthesized

<400> SEQUENCE: 37
gtagccaata gcgttaataa ta                                               22

<210> SEQ ID NO 38
<211> LENGTH: 23
<212> TYPE: DNA
<213> ORGANISM: Artificial
<220> FEATURE:
<223> OTHER INFORMATION: Completely Synthesized

<400> SEQUENCE: 38
gatgctaatg atatatttcc ata                                              23

<210> SEQ ID NO 39
<211> LENGTH: 23
<212> TYPE: DNA
<213> ORGANISM: Artificial
<220> FEATURE:
<223> OTHER INFORMATION: Completely Synthesized

```
<400> SEQUENCE: 39
acrttctatt gtgaaggtgc ytc                                              23

<210> SEQ ID NO 40
<211> LENGTH: 21
<212> TYPE: DNA
<213> ORGANISM: Artificial
<220> FEATURE:
<223> OTHER INFORMATION: Completely Synthesized

<400> SEQUENCE: 40
atatttcaag cyccatagta g                                                21

<210> SEQ ID NO 41
<211> LENGTH: 18
<212> TYPE: DNA
<213> ORGANISM: Artificial
<220> FEATURE:
<223> OTHER INFORMATION: Completely Synthesized

<400> SEQUENCE: 41
gagtgcccta atccagtg                                                    18

<210> SEQ ID NO 42
<211> LENGTH: 20
<212> TYPE: DNA
<213> ORGANISM: Artificial
<220> FEATURE:
<223> OTHER INFORMATION: Completely Synthesized

<400> SEQUENCE: 42
ctgtgttctt aggtattatg                                                  20

<210> SEQ ID NO 43
<211> LENGTH: 22
<212> TYPE: DNA
<213> ORGANISM: Artificial
<220> FEATURE:
<223> OTHER INFORMATION: Completely Synthesized

<400> SEQUENCE: 43
attgcttacg gaggtgattt tg                                               22

<210> SEQ ID NO 44
<211> LENGTH: 21
<212> TYPE: DNA
<213> ORGANISM: Artificial
<220> FEATURE:
<223> OTHER INFORMATION: Completely Synthesized

<400> SEQUENCE: 44
atcatttcca tgtagagttg c                                                21

<210> SEQ ID NO 45
<211> LENGTH: 24
<212> TYPE: DNA
<213> ORGANISM: Artificial
<220> FEATURE:
<223> OTHER INFORMATION: Completely Synthesized

<400> SEQUENCE: 45
tcttytgcac cctartcyat ttga                                             24

<210> SEQ ID NO 46
```

```
<211> LENGTH: 21
<212> TYPE: DNA
<213> ORGANISM: Artificial
<220> FEATURE:
<223> OTHER INFORMATION: Completely Synthesized

<400> SEQUENCE: 46
gtycaattct accttctatg a                                              21

<210> SEQ ID NO 47
<211> LENGTH: 21
<212> TYPE: DNA
<213> ORGANISM: Artificial
<220> FEATURE:
<223> OTHER INFORMATION: Completely Synthesized

<400> SEQUENCE: 47
gacttgraga ggtacrtttt c                                              21

<210> SEQ ID NO 48
<211> LENGTH: 21
<212> TYPE: DNA
<213> ORGANISM: Artificial
<220> FEATURE:
<223> OTHER INFORMATION: Completely Synthesized

<400> SEQUENCE: 48
gacttggaga agtacatttt c                                              21

<210> SEQ ID NO 49
<211> LENGTH: 21
<212> TYPE: DNA
<213> ORGANISM: Artificial
<220> FEATURE:
<223> OTHER INFORMATION: Completely Synthesized

<400> SEQUENCE: 49
gcattrcttc tctgaatgaa t                                              21

<210> SEQ ID NO 50
<211> LENGTH: 22
<212> TYPE: DNA
<213> ORGANISM: Artificial
<220> FEATURE:
<223> OTHER INFORMATION: Completely Synthesized

<400> SEQUENCE: 50
agttagttgt aatccactat ac                                             22

<210> SEQ ID NO 51
<211> LENGTH: 22
<212> TYPE: DNA
<213> ORGANISM: Artificial
<220> FEATURE:
<223> OTHER INFORMATION: Completely Synthesized

<400> SEQUENCE: 51
attttgcgat caatatacac at                                             22

<210> SEQ ID NO 52
<211> LENGTH: 20
<212> TYPE: DNA
<213> ORGANISM: Artificial
<220> FEATURE:
<223> OTHER INFORMATION: Completely Synthesized

<400> SEQUENCE: 52
```
gatgatgatg atgatgatga                                                   20

<210> SEQ ID NO 53
<211> LENGTH: 22
<212> TYPE: DNA
<213> ORGANISM: Artificial
<220> FEATURE:
<223> OTHER INFORMATION: Completely Synthesized

<400> SEQUENCE: 53
caattatayc ctatttactc aa                                                22

<210> SEQ ID NO 54
<211> LENGTH: 22
<212> TYPE: DNA
<213> ORGANISM: Artificial
<220> FEATURE:
<223> OTHER INFORMATION: Completely Synthesized

<400> SEQUENCE: 54
ttgagtaaat aggrtataat tg                                                22

<210> SEQ ID NO 55
<211> LENGTH: 31
<212> TYPE: DNA
<213> ORGANISM: Artificial
<220> FEATURE:
<223> OTHER INFORMATION: Completely Synthesized

<400> SEQUENCE: 55
tttttaatta accyagaatc gggtaattttt t                                     31

<210> SEQ ID NO 56
<211> LENGTH: 21
<212> TYPE: DNA
<213> ORGANISM: Artificial
<220> FEATURE:
<223> OTHER INFORMATION: Completely Synthesized

<400> SEQUENCE: 56
ttacccgatt ctrggttaat t                                                 21

<210> SEQ ID NO 57
<211> LENGTH: 51
<212> TYPE: DNA
<213> ORGANISM: Artificial
<220> FEATURE:
<223> OTHER INFORMATION: Completely Synthesized

<400> SEQUENCE: 57
tttttttttt tttttctra cagctttgrc aagtttttt tttttttttt t                  51

<210> SEQ ID NO 58
<211> LENGTH: 21
<212> TYPE: DNA
<213> ORGANISM: Artificial
<220> FEATURE:
<223> OTHER INFORMATION: Completely Synthesized

<400> SEQUENCE: 58
aaacttgyca aagctgtyag a                                                 21

<210> SEQ ID NO 59
<211> LENGTH: 19
<212> TYPE: DNA

```
<213> ORGANISM: Artificial
<220> FEATURE:
<223> OTHER INFORMATION: Completely Synthesized

<400> SEQUENCE: 59
tatcagyccc attgcctat                                                19

<210> SEQ ID NO 60
<211> LENGTH: 19
<212> TYPE: DNA
<213> ORGANISM: Artificial
<220> FEATURE:
<223> OTHER INFORMATION: Completely Synthesized

<400> SEQUENCE: 60
ataggcaatg ggrctgata                                                19

<210> SEQ ID NO 61
<211> LENGTH: 20
<212> TYPE: DNA
<213> ORGANISM: Artificial
<220> FEATURE:
<223> OTHER INFORMATION: Completely Synthesized

<400> SEQUENCE: 61
cccyttaact gcgaataaac                                               20

<210> SEQ ID NO 62
<211> LENGTH: 20
<212> TYPE: DNA
<213> ORGANISM: Artificial
<220> FEATURE:
<223> OTHER INFORMATION: Completely Synthesized

<400> SEQUENCE: 62
gtttattcgc agttaarggg                                               20

<210> SEQ ID NO 63
<211> LENGTH: 59
<212> TYPE: DNA
<213> ORGANISM: Artificial
<220> FEATURE:
<223> OTHER INFORMATION: Completely Synthesized

<400> SEQUENCE: 63
tttttttttt tttttttttt cctatttgct acaacagtgt tttttttttt tttttttt    59

<210> SEQ ID NO 64
<211> LENGTH: 19
<212> TYPE: DNA
<213> ORGANISM: Artificial
<220> FEATURE:
<223> OTHER INFORMATION: cactgttgtagcaaatagg

<400> SEQUENCE: 64
cactgttgta gcaaatagg                                                19

<210> SEQ ID NO 65
<211> LENGTH: 20
<212> TYPE: DNA
<213> ORGANISM: Artificial
<220> FEATURE:
<223> OTHER INFORMATION: Completely Synthesized

<400> SEQUENCE: 65
argacgtcac ctctaaacga                                               20
```

<210> SEQ ID NO 66
<211> LENGTH: 20
<212> TYPE: DNA
<213> ORGANISM: Artificial
<220> FEATURE:
<223> OTHER INFORMATION: Completely Synthesized

<400> SEQUENCE: 66
tcgtttagag gtgacgtcyt                                                    20

<210> SEQ ID NO 67
<211> LENGTH: 23
<212> TYPE: DNA
<213> ORGANISM: Artificial
<220> FEATURE:
<223> OTHER INFORMATION: Completely Synthesized

<400> SEQUENCE: 67
cttgttaayg atgyaatatc rat                                                23

<210> SEQ ID NO 68
<211> LENGTH: 23
<212> TYPE: DNA
<213> ORGANISM: Artificial
<220> FEATURE:
<223> OTHER INFORMATION: Completely Synthesized

<400> SEQUENCE: 68
atygatattr catcrttaac aag                                                23

<210> SEQ ID NO 69
<211> LENGTH: 44
<212> TYPE: DNA
<213> ORGANISM: Artificial
<220> FEATURE:
<223> OTHER INFORMATION: Completely Synthesized

<400> SEQUENCE: 69
tttttttttt tcaaatrgay tagggtgcar aagattttt tttt                          44

<210> SEQ ID NO 70
<211> LENGTH: 24
<212> TYPE: DNA
<213> ORGANISM: Artificial
<220> FEATURE:
<223> OTHER INFORMATION: Completely Synthesized

<400> SEQUENCE: 70
tcttytgcac cctartcyat ttga                                               24

<210> SEQ ID NO 71
<211> LENGTH: 22
<212> TYPE: DNA
<213> ORGANISM: Artificial
<220> FEATURE:
<223> OTHER INFORMATION: Completely Synthesized

<400> SEQUENCE: 71
gtatagtgga ttacaactaa ct                                                 22

<210> SEQ ID NO 72
<211> LENGTH: 22
<212> TYPE: DNA
<213> ORGANISM: Artificial
<220> FEATURE:

```
-continued

<223> OTHER INFORMATION: Completely Synthesized

<400> SEQUENCE: 72
agttagttgt aatccactat ac                                              22

<210> SEQ ID NO 73
<211> LENGTH: 22
<212> TYPE: DNA
<213> ORGANISM: Artificial
<220> FEATURE:
<223> OTHER INFORMATION: Completely Synthesized

<400> SEQUENCE: 73
caattatayc ctatttactc aa                                              22

<210> SEQ ID NO 74
<211> LENGTH: 20
<212> TYPE: DNA
<213> ORGANISM: Artificial
<220> FEATURE:
<223> OTHER INFORMATION: Completely Synthesized

<400> SEQUENCE: 74
gatgatgatg atgatgatga                                                 20
```